(12) United States Patent
Catozzi et al.

(10) Patent No.: US 9,522,869 B2
(45) Date of Patent: *Dec. 20, 2016

(54) PROCESS FOR PREPARING CINACALCET HYDROCHLORIDE

(71) Applicant: ZACH SYSTEM S.P.A., Bresso (IT)

(72) Inventors: Nicola Catozzi, Sovizzo (IT); Livius Cotarca, Cervignano del Friuli (IT); Johnny Foletto, Arcole (IT); Massimiliano Forcato, Galzignano Terme (IT); Roberto Giovanetti, Schio (IT); Giorgio Soriato, Caldiero (IT); Massimo Verzini, Caldiero (IT)

(73) Assignee: ZACH SYSTEM S.P.A., Bresso (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/303,977

(22) Filed: Jun. 13, 2014

(65) Prior Publication Data

US 2014/0296574 A1 Oct. 2, 2014

Related U.S. Application Data

(63) Continuation of application No. 13/201,633, filed as application No. PCT/EP2010/051900 on Feb. 16, 2010, now abandoned.

(30) Foreign Application Priority Data

Feb. 19, 2009 (EP) ...................... 09153208

(51) Int. Cl.
| | |
|---|---|
| *C07C 209/70* | (2006.01) |
| *C07C 211/30* | (2006.01) |
| *C07C 221/00* | (2006.01) |
| *C07C 211/28* | (2006.01) |
| *C07C 303/28* | (2006.01) |
| *C07C 305/12* | (2006.01) |

(52) U.S. Cl.
CPC ........... *C07C 209/70* (2013.01); *C07C 211/28* (2013.01); *C07C 211/30* (2013.01); *C07C 221/00* (2013.01); *C07C 303/28* (2013.01); *C07C 305/12* (2013.01)

(58) Field of Classification Search
None
See application file for complete search history.

(56) References Cited

U.S. PATENT DOCUMENTS

| | | | |
|---|---|---|---|
| 8,614,353 B2 * | 12/2013 | Catozzi et al. ........... | 564/343 |
| 8,637,708 B2 * | 1/2014 | Catozzi et al. ........... | 564/366 |
| 2007/0260091 A1 * | 11/2007 | Lifshitz-Liron ........... | 564/374 |
| 2011/0207965 A1 | 8/2011 | Catozzi et al. | |

FOREIGN PATENT DOCUMENTS

| | | |
|---|---|---|
| WO | 2007/127449 A1 | 11/2007 |
| WO | 2009/002427 A2 | 12/2008 |
| WO | 2009/153814 A1 | 12/2009 |
| WO | 2010/015935 A2 | 2/2010 |
| WO | 2010/049293 A2 | 5/2010 |

OTHER PUBLICATIONS

Stuetz, A., et al., "Synthesis and Structure-Activity Relationships of Naftifine-Related Allylamine Antimycotics" Journal of Medicinal Chemistry, American Chemical Society, Washington, US LNKD-DOI:10.1021/JM00151A019, vol. 29, No. 1, Jan. 1, 1986, pp. 112-125, XP002037080, ISSN: 0022-2623.

(Continued)

*Primary Examiner* — Clinton Brooks
(74) *Attorney, Agent, or Firm* — Silvia Salvadori, P.C.; Silvia Salvadori

(57) ABSTRACT

A process for preparing N-[(1R)-1-(1-naphthyl)ethyl]-3-[3-(trifluoromethyl)-phenyl]propan-1-amine hydrochloride salt of formula (I)

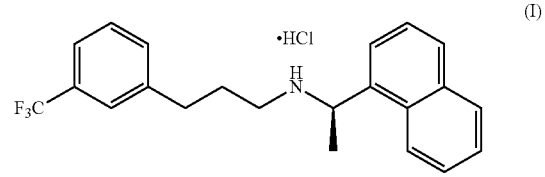

(I)

i.e. Cinacalcet hydrochloride and its intermediates of formulae (VII) and (VIII)

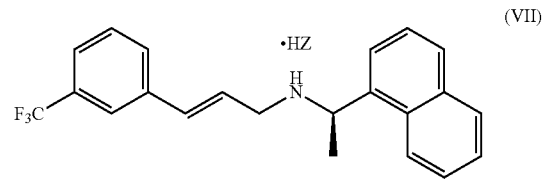

(VII)

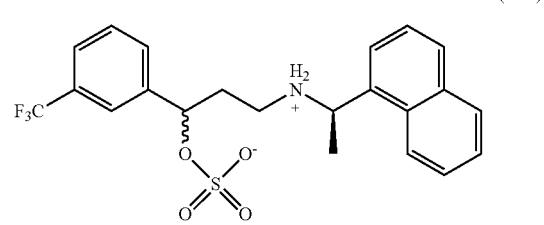

(VIII)

wherein Z is chloride or another pharmaceutically acceptable anionic counterion.

12 Claims, No Drawings

(56) References Cited

OTHER PUBLICATIONS

Thiel, et al., "Practical Synthesis of the Calcimimetic agent, Cinacalcet" Tetrahedron Letters, Elsevier, Amsterdam, NL LNKL-DOI:10.1016/J.TETLET.2007.11.030, vol. 49, No. 1, Nov. 26, 20007, pp. 13-15, XP022374243, ISSN: 0040-4039.
ISR and Written Opinion of PCT/EP2010/051900 dated Aug. 31, 2010.
Serajuddin A., "Salt Formation to Improve Drug Solubility" Advanced Drug Delivery Reviews 59 (2007) 603-616.

* cited by examiner

PROCESS FOR PREPARING CINACALCET HYDROCHLORIDE

This application is a continuation application of U.S. Ser. No. 13/201,633 filed on Aug. 16, 2011, which is a U.S. national stage of PCT/EP2010/051900 filed on Feb. 16, 2010 which claims priority to and the benefit of European Application No. 09153208.5 filed on Feb. 19, 2009, the contents of which are incorporated herein by reference in their entireties.

The invention relates to a process for preparing the active product ingredient Cinacalcet hydrochloride (CNC.HCl), namely N-[(1R)-1-(1-naphthyl)ethyl]-3-[3-(trifluoromethyl)phenyl]propan-1-amine hydrochloride of formula (I)

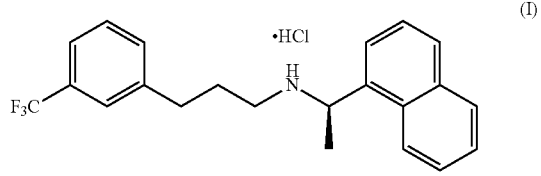 [SMILES: C[C@@H](NCCCc1cccc(C(F)(F)F)c1)c1cccc2ccccc12 ; Cl]

CNC.HCl, marketed as MIMPARA™ in the European Union, is a calcimimetic agent that decreases the secretion of parathyroid hormone by activating calcium receptors.

MIMPARA™ is approved for the treatment of secondary hyperparathyroidism (SHPT) in patients with chronic kidney disease receiving dialysis and for the treatment of primary hyperparathyroidism (PHPT) in patients for whom parathyroidectomy is not clinically appropriate or contraindicated.

U.S. Pat. No. 6,011,068 discloses a class of arylalkylamines comprising generically Cinacalcet (CNC) and salts thereof. U.S. Pat. No. 6,211,244 describes specifically Cinacalcet or a pharmaceutically acceptable salt or complex thereof as the compound 22J, but it does not provide any specific examples for the preparation of Cinacalcet and/or Cinacalcet hydrochloride.

Most prior art processes for preparing the hydrochloride salt of Cinacalcet typically comprise: providing a solution of Cinacalcet in a solvent; treating said solution with an amount of hydrochloric acid sufficient to convert Cinacalcet to its hydrochloride salt; precipitating said hydrochloride salt and recovering said salt.

For example, U.S. Pat. No. 7,247,751 generically describes a method of preparing Cinacalcet hydrochloride crystalline form I, which comprises providing a solution of Cinacalcet base in a solvent in which Cinacalcet hydrochloride has a low solubility; acidifying the solution with hydrochloric acid to obtain a reaction mixture; maintaining the reaction mixture to obtain a precipitate; and recovering the precipitated Cinacalcet hydrochloride crystalline Form I. Preferably, the solvent is selected from the group consisting of acetone, ethanol, isopropyl alcohol, and methanol. The preparation of Cinacalcet hydrochloride crystalline form I from Cinacalcet is specifically described in Example 5 of U.S. Pat. No. 7,247,751, wherein a solution of Cinacalcet was formed by dissolving Cinacalcet base in absolute ethanol, hydrochloric acid was added drop-wise to the solution and the resulting mixture was stirred at ambient temperature, producing a precipitate. The product was isolated by filtration and dried in a vacuum, yielding Cinacalcet hydrochloride crystalline form I. Example 9 of WO 2008/058235 discloses the preparation of Cinacalcet hydrochloride starting from N-[(1R)-1-(1-napthyl)ethyl]-3-(3-trifluoromethyl)phenyl]propanamide, without isolating Cinacalcet free base.

WO 2008/058235 provides a process for making Cinacalcet hydrochloride from Cinacalcet that includes the steps of: providing a solution of Cinacalcet in an alcohol or alkyl acetate; treating the solution of the free base with an hydrochloric acid to convert the free base to the hydrochloride salt; adding an anti-solvent to solution containing the hydrochloride salt to precipitate it in the form of a solid; and isolating the precipitated solid to obtain the Cinacalcet hydrochloride. WO 2008/058235 also describes a process for making Cinacalcet hydrochloride by providing a solution of an acid addition salt of Cinacalcet other than Cinacalcet hydrochloride, treating said solution with an amount of hydrochloric acid sufficient to convert the acid addition salt to said hydrochloride salt; and isolating said cinacalcet hydrochloride.

U.S. Pat. No. 7,393,967 discloses a process for preparing Cinacalcet hydrochloride via coupling of 3-bromotrifluorotoluene with (R)—N-(1-(naphthalen-1-yl)ethyl)prop-2-en-1-amine in the presence of a catalyst and at least one base to obtain (R,E)-N-(1-(naphthalen-1-yl)ethyl)-3-(3-(trifluoromethyl)phenyl)prop-2-en-1-amine (Example 1, Step 1), reducing the unsaturated Cinacalcet to obtain Cinacalcet (example 1, Step 2), and converting Cinacalcet to Cinacalcet hydrochloride (Example 2 or Example 3) as depicted in the following Scheme 1:

Scheme 1

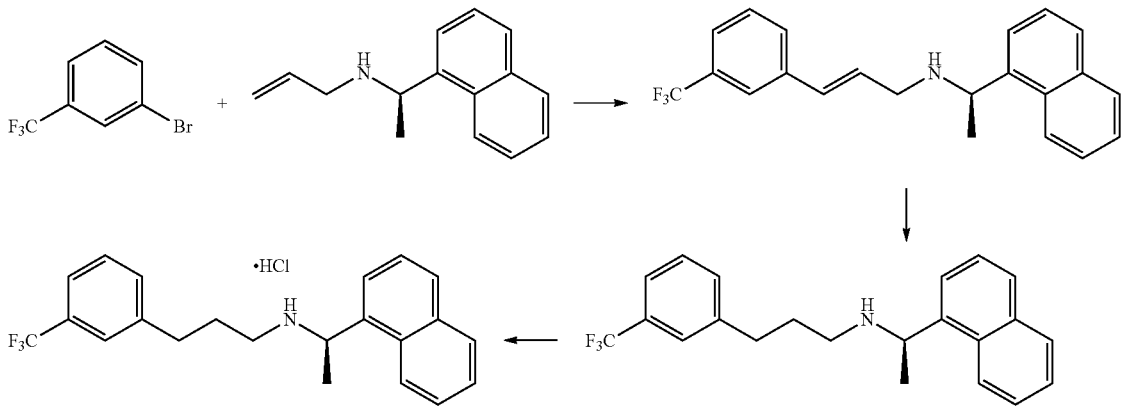

The present invention provides, in a first aspect, a novel and efficient method that leads to a Cinacalcet salt, especially the hydrochloride, which is convenient for the industrial scale and provides the desired product in good yields. In particular, the inventors found that Cinacalcet hydrochloride can be advantageously obtained with a process, which does not contemplate the isolation of Cinacalcet free base.

Accordingly, it is an object of the present invention to provide a method for preparing Cinacalcet hydrochloride of formula (I)

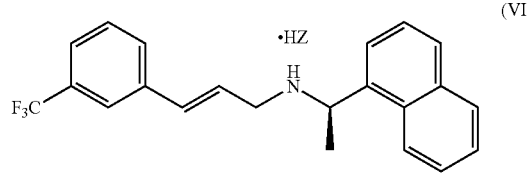

(I)

which comprises the steps of:

e) reducing a compound of formula (VII)

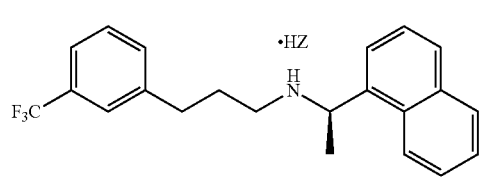

(VII)

wherein Z is chloride or another pharmaceutically acceptable anionic counterion, to obtain a compound of formula (Ia)

(Ia)

wherein Z is as defined above and, when in a compound of formula (Ia) Z is a pharmaceutically acceptable anionic counterion different from chloride, f) converting said compound of formula (Ia) to Cinacalcet hydrochloride of formula (I).

A "pharmaceutically acceptable anionic counterion" Z refers to a negatively charged molecule or atom that is balanced by the positively charged protonated Cinacalcet. A pharmaceutically acceptable anionic counterion may be organic or inorganic. For example, representative pharmaceutically acceptable anionic counterions include chloride, bromide, bisulfate (hydrogen sulfate), methanesulfonate, p-toluenesulfonate, phosphate, hydrogenphosphate, oxalate, formate, acetate, citrate, tartrate, succinate, maleate and malonate. Chloride, bisulfate, p-toluenesulfonate, tartrate and succinate are preferred; chloride and bisulfate are more preferred.

As an example, the compound of formula (VII) wherein Z is chloride is the compound of formula (VIIa),

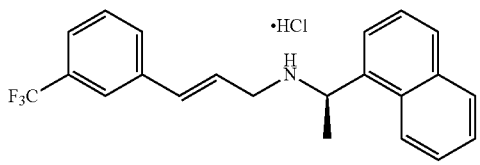

(VIIa)

the compound of formula (VII) wherein Z is bisulfate is the compound of formula (VIIb),

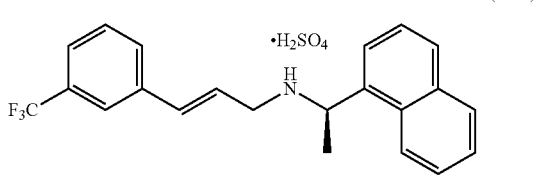

(VIIb)

the compound of formula (VII) wherein Z is tartrate is the compound of formula (VIIc),

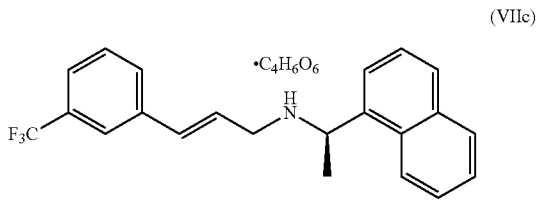 [SMILES: C[C@@H](NC/C=C/c1cccc(C(F)(F)F)c1)c1cccc2ccccc12 ; "·C4H6O6"]

(VIIc)

the compound of formula (VII) wherein Z is succinate is the compound of formula (VIId),

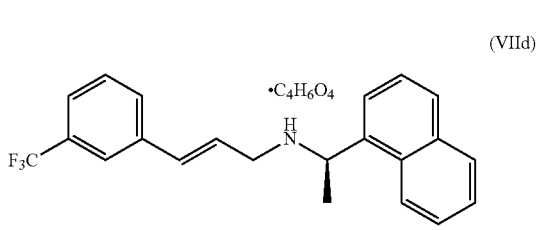

(VIId)

and the compound of formula (VII) wherein Z is p-toluenesulfonate is the compound of formula (VIIe)

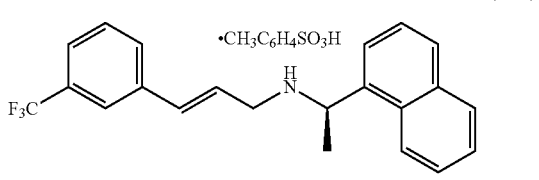

(VIIe)

In a preferred aspect, the present invention is directed to a method for preparing Cinacalcet hydrochloride of formula (I), which comprises the step of reducing the compound of formula (VIIa) as defined above.

In another aspect, the method according to the present invention further comprises obtaining the compound of formula (VIIa) as defined above, by a process which comprises the step of:
g) converting a compound of formula (VII) wherein Z is a pharmaceutically acceptable anionic counterion different from chloride.

In a further preferred aspect, the method according to the present invention further comprises obtaining the compound of formula (VIIa) as defined above, by a process which comprises the step of:
g) converting a compound of formula (VIIb) as defined above.

The reduction according to the above step e) can be carried out starting from a compound of formula (VII), particularly the compound of formula (VIIa), by catalytic hydrogenation, i.e. with molecular hydrogen in the presence of a catalyst. The catalytic hydrogenation may be performed by any method known to a person skilled in the art. For example, a compound of formula (VII), particularly the compound of formula (VIIa), may be dissolved in a in a suitable solvent and exposed to $H_2$ pressure, in the presence of a catalyst such as, for example, Pd/C, $PtO_2$ (Adam's catalysts), Raney nickel or $PdCl_2$. When the catalyst is selected from Pd/C, $PtO_2$ or $PdCl_2$, the $H_2$ pressure is chosen in the range of from 0.5 to 5 atm, while when the catalyst is Raney nickel, the $H_2$ pressure is chosen in a higher range from 4 to 70 atm. The suitable solvent can be selected from the group consisting of a $C_2$-$C_5$ nitrile such as, for example, acetonitrile; a linear or branched $C_1$-$C_4$ alcohol such as, for example, methyl, ethyl, n-propyl, iso-propyl, n-butyl, sec-butyl or tert-butyl alcohol; a linear or branched $C_3$-$C_9$ ketone such as, for example, methylethyl or methylisobutyl ketone; a linear or branched $C_3$-$C_7$ ester such as, for example, ethyl, iso-propyl or n-butyl acetate; toluene and mixtures thereof. Preferably, the solvent can be selected from the group consisting of methanol, ethanol, isopropanol, ethyl acetate and mixtures thereof, more preferably the solvent is methanol. Typically, the hydrogenation is carried out over a period of about 1 hour to 96 hours. Reaction temperature may range from 0° to 50° C., preferably from 10° to 30° C., more preferably at 20° C.

The conversion of a compound of formula (Ia) into Cinacalcet hydrochloride of formula (I) according to the above step f), and the conversion of a compound of a formula (VII) where Z is an anionic counterion different from chloride into a compound of formula (VIIa) according to step g), can be carried out dissolving a compound of formula (Ia) as defined above or, respectively, a compound (VII) as defined above, in a solvent selected from water; a linear or branched $C_1$-$C_4$ alcohol such as, for example, methyl, ethyl, n-propyl, iso-propyl, n-butyl, sec-butyl or tert-butyl alcohol; a linear or branched $C_4$-$C_8$ ester such as, for example, ethyl acetate, isopropyl acetate or n-butyl acetate; or mixtures thereof, at a temperature ranging from room temperature to the boiling point of the selected solvent, or mixture of solvents, and treating said compounds with aqueous hydrochloric acid. A moderately high excess of hydrochloric acid (2-10 equiv.) has to be used when the acid HZ is a stronger acid than hydrochloric acid.

The conversion of a compound of formula (VII) where Z is an anionic counterion different from chloride into a compound of formula (VIIa) according to step g), can be alternatively carried out suspending a compound of formula (VII) as defined above in a solvent selected from toluene; a linear or branched $C_4$-$C_8$ ether such as, for example, methyl tert-butyl ether, diisopropyl ether or di-n-butyl ether; a linear or branched $C_4$-$C_8$ ester such as, for example, ethyl acetate, isopropyl acetate or n-butyl acetate; or mixtures thereof, and treating said compound with an aqueous base, such as for example sodium hydroxide, sodium or potassium carbonate, sodium or potassium hydrogen carbonate, sodium or potassium phosphate, extracting the so obtained unsaturated Cinacalcet free base (CNC-ene free base) in the organic layer and precipitating the compound of formula (VIIa) from the organic solvent upon treatment with aqueous hydrochloric acid.

A compound of formula (VII) can be obtained converting (R,E)-N-(1-(naphthalen-1-yl)ethyl)-3-(3-(trifluoromethyl) phenyl)prop-2-en-1-amine (CNC-ene free base) by any method known to a person skilled in the art. CNC-ene free base can be prepared, for example, as depicted in the U.S. Pat. No. 7,393,967, Example 1, Step 1, or following the teachings of the ZaCh System co-pending European patent application No. 08167762.7.

Alternatively, a compound of formula (VII), wherein Z is a pharmaceutically acceptable anionic counterion different from chloride, can be obtained with a novel method which comprises the step of:
j) eliminating sulfuric acid from the compound of formula (VIII)

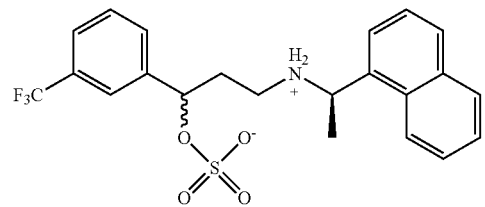

(VIII)

wherein the wavy line represents a bond connected to carbon having R or S configuration, with a strong acid, neutralizing and acidifying with the proper acid HZ, wherein Z is a pharmaceutically acceptable anionic counterion different from chloride.

In a preferred aspect, the compound of formula (VIIb) as defined above can be obtained by a method which comprises the step of:
j) eliminating sulfuric acid from the compound of formula (VIII) as defined above with a strong acid, neutralizing and acidifying with $H_2SO_4$.

It is therefore another object of the present invention to provide a method for preparing Cinacalcet hydrochloride of formula (I) as defined above, which further comprises preparing a compound of formula (VII) wherein Z is a pharmaceutically acceptable anionic counterion different from chloride, with a process which comprises the above step j).

The elimination of sulfuric acid according to the above step j) can be carried out by reacting the compound of formula (VIII) with a strong acid such as, for example, sulfuric or phosphoric acid, preferably concentrated sulfuric acid, with or without a solvent selected from high boiling toluene, n-butyl acetate and n-butyl ether, preferably n-butyl acetate, and at a temperature ranging from room temperature to the refluxing temperature of the selected solvent, preferably 115° C. Once the reaction has gone to completion, a compound (VII) wherein Z is a pharmaceutically acceptable anionic counterion different from chloride, can be obtained by any work up method known to a person skilled in the art. For example, a compound of formula (VII) as defined above can be isolated by neutralizing the acidic reaction mixture with an aqueous base, preferably sodium hydroxide, extracting the compound (R,E)-N-(1-(naphthalen-1-yl)ethyl)-3-(3-(trifluoromethyl)phenyl)prop-2-en-1-amine (CNC-ene free base) in organic phase, preferably in n-butyl acetate, acidifying said organic phase with the proper acid HZ, wherein Z is a pharmaceutically acceptable anionic counterion different from chloride, preferably bisulfate, and precipitating the corresponding compound of formula (VII).

It is a further object of the present invention the Cinacalcet intermediate of formula (VIII) as defined above.

The compound of formula (VIII) as defined above can be obtained with a novel method which comprises the step of:
k) reducing the compound of formula (V)

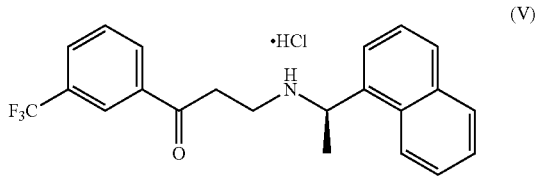 [SMILES: C[C@@H](NCCC(=O)c1cccc(C(F)(F)F)c1)c1cccc2ccccc12 ; Cl]
(V)

to the corresponding benzylic alcohol of formula (Va)

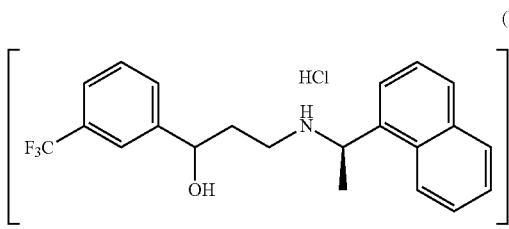
(Va)

in the presence of a reducing agent or by mean of a catalytic hydrogenation process, and
l) converting the compound of formula (Va) into the sulfate ester of formula (VIII). In the formula (Va), [ ] means that the compound of formula (Va) can be isolated or not from the reaction mixture.

The reduction of the compound of formula (V) according to the above step k) can be carried out with suitable reducing agents including sodium borohydride; lithium borohydride; diisobutyl aluminium hydride; and 1,1,3,3-tetramethyldisiloxane in combination with a Lewis acid. Suitable reduction catalysts, which can be used with gaseous hydrogen, include Pd/C, PtO$_2$ (Adam's catalysts), Raney nickel and PdCl$_2$. The reaction can be carried out in a solvent selected from, for example, water; a linear or branched C$_1$-C$_4$ alcohol such as, for example, methyl, ethyl, n-propyl, iso-propyl, n-butyl or sec-butyl alcohol; a linear or branched C$_4$-C$_8$ ether such as 1,2-dimethoxyethane, 2-methoxyethyl ether, diisopropyl ether, di-n-butyl ether, methyl tert-butyl ether, tetrahydrofuran or 1,4-dioxane; or a mixture thereof, depending on the reducing agent; at a temperature ranging between −10° to 40° C., over a period of about 0.5 to 10 hours. When the catalyst Pd/C, PtO$_2$ or PdCl$_2$ is used, the H$_2$ pressure is typically 1 atm. When Raney nickel is used, the H$_2$ pressure is moderately high (—1000 psi). Typically, the hydrogenation is carried out over a period of about 5 to about 24 hours. When the reduction is carried out upon catalytic transfer hydrogenation (CTH) conditions, suitable hydrogen-bearing feed materials such as, for example, formic acid, ammonium formate or sodium formate, preferably ammonium formate or sodium formate are employed. In order to activate the hydrogen-bearing material as hydrogen donor, a catalyst as defined above is employed: the catalyst promotes the hydrogen transfer from hydrogen-bearing feed material to the substrate. CTH may be performed by any method known to a person skilled in the art. In particular, when CTH techniques are used in the reaction under step k), the compound of formula (V) is dissolved in a solvent selected from for example, toluene, acetic acid and a C$_1$-C$_5$ alcohol as defined above, preferably ethyl alcohol, in the presence of formic acid, ammonium formate or sodium formate, preferably ammonium formate or sodium formate, at refluxing temperature of the selected solvent, over a period of about 5 to 48 hours. In a most preferred embodiment, sodium borohydride in methanol at a temperature ranging from −10° C. to 10° C. is used.

Once the intermediate benzylic alcohol of formula (Va) is formed, either it is isolated or not, it can be converted into the sulfate ester of formula (VIII) according to the above step l) by treatment with sulfuric acid and acetic anhydride, in a solvent selected from acetonitrile, a C$_4$-C$_8$ ether as defined above, a linear or branched C$_4$-C$_6$ ester, such as, ethyl, iso-propyl, n-butyl acetate, or a mixture thereof, at a temperature ranging from 0°-50° C., most preferably at 25° C.

It is therefore another object of the present invention to provide a method for preparing Cinacalcet hydrochloride of formula (I) as defined above, which further comprises preparing the compound of formula (VIII), with a process which comprises the above steps k) and l), with or without the isolation of the intermediate compound of formula (Va).

For clarity's sake, the above processes may be illustrated by the following Scheme 2:

Scheme 2

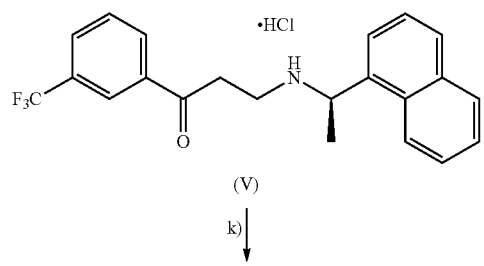
(V)

k)↓

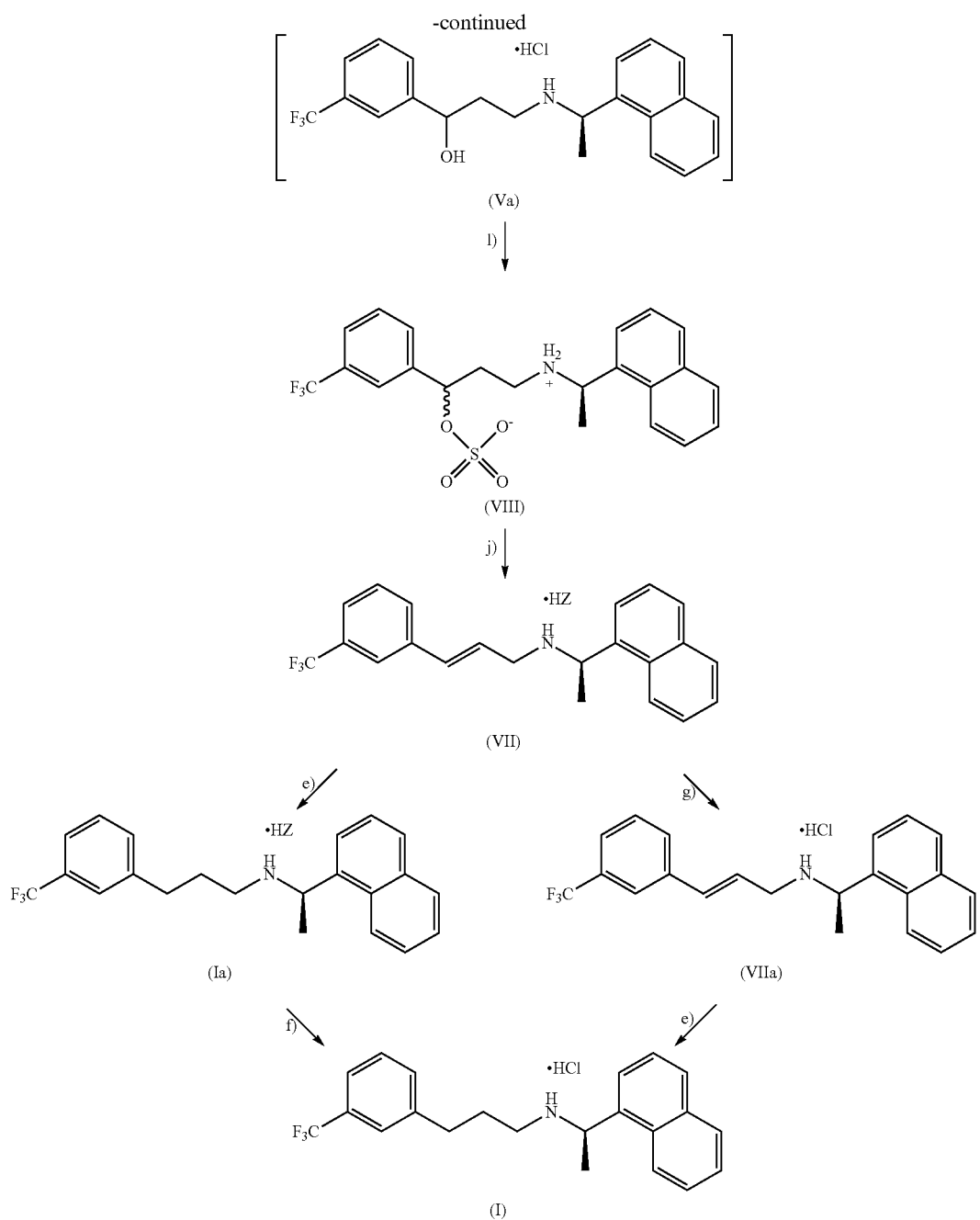
In a particular aspect, the present invention provides a method for preparing Cinacalcet hydrochloride of formula (I)
which comprises the steps of
k) reducing the compound of formula (V)
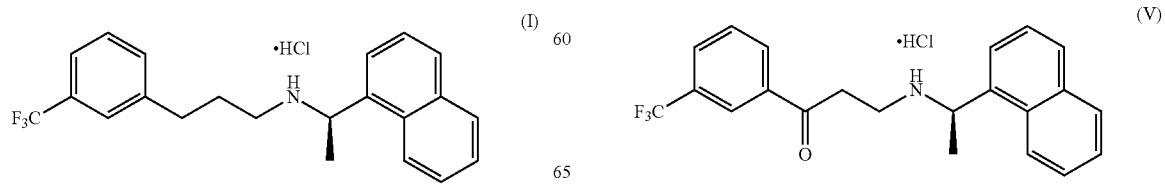

to the corresponding benzylic alcohol of formula (Va)

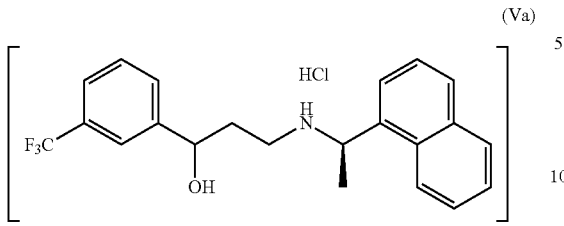

wherein [ ] means that the compound of formula (Va) can be isolated or not from the reaction mixture, in the presence of a reducing agent or by mean of a catalytic hydrogenation process, l) converting the compound of formula (Va) into the sulphate ester of formula (VIII)

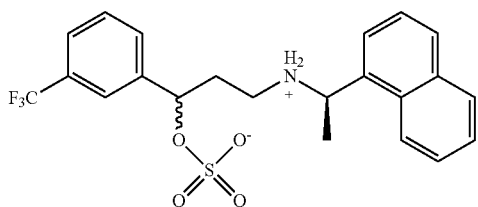

wherein the wavy line represents a bond connected to carbon having R or S configuration, j) eliminating sulfuric acid from the compound of formula (VIII) with a strong acid, neutralizing and acidifying with $H_2SO_4$ to give the compound of formula (VIIb)

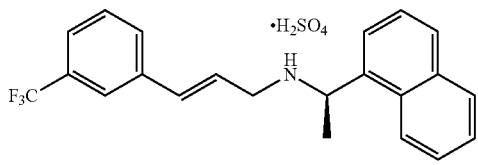

g) converting the compound (VIIb) into the compound (VIIa) and

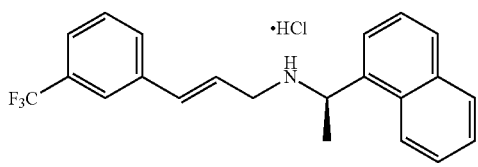

e) reducing the compound (VIIa) to obtain Cinacalcet hydrochloride of formula (I).

The compound of formula (V) as defined above can be prepared according to the methods described in ZaCh System's co-pending European patent application No. 08167762.7, which comprises the step of:

a) reacting 3-(trifluoromethyl)acetophenone of formula (II)

with (R)-(1-naphthyl)ethylamine of formula (III), optionally in the hydrochloride form,

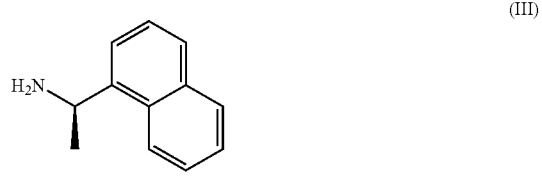

in the presence of formaldehyde and hydrochloric acid to give the compound of formula (V)

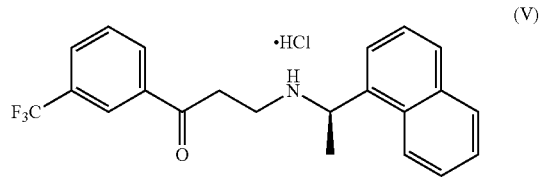 [SMILES: C[C@@H](NCCC(=O)c1cccc(C(F)(F)F)c1)c1cccc2ccccc12 ; Cl]

In a preferred aspect of the present invention, the reaction under the above step a) is carried out with (R)-(1-naphthyl)ethylamine hydrochloride salt.

It is therefore a further object of the present invention to provide a method for preparing Cinacalcet hydrochloride of formula (I) as defined above, which further comprises preparing the compound of formula (V), with a process which comprises the above step a).

According to ZaCh System co-pending European patent application No. 08167762.7, the compound of formula (V) can also be prepared with a process which comprises the steps of:

b) reacting the compound of formula (II) as defined above
   (i) with a compound of formula
   $HNR_1R_2$,
   wherein $R_1$ and $R_2$ represent, independently, hydrogen or $C_1$-$C_5$ alkyl, provided that when one of $R_1$ and $R_2$ is hydrogen, the other is not hydrogen; or
   wherein $R_1$ and $R_2$ together form a $C_4$-$C_7$ alkyl bridge, so that with the inclusion of the nitrogen atom to which they are linked a heterocycle is formed, wherein one —$CH_2$— group of the $C_4$-$C_7$ alkyl bridge, can be replaced by —O—, in the presence of formaldehyde; or
   (ii) with a N-methyl-N-methylenemethanaminium halide of formula

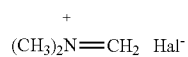

wherein Hal is a halogen atom, to obtain the compound of formula (IV)

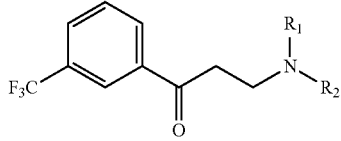

(IV)

wherein $R_1$ and $R_2$ are as defined above;
c) alkylating the compound of formula (IV) with an alkylating agent selected from the group of compounds of formula:
$R_3$—X, $CO(OR_3)_2$, $SO_2(OR_3)_2$, $PO(OR_3)_3$, $CH_3PO(OR_3)_2$ and $(4-NO_2C_6H_4O)PO(OR_3)_2$, wherein $R_3$ is $C_1$-$C_4$ alkyl and X is I, Br, $OSO_2CF_3$ or $OSO_2F$, to obtain a compound of formula (IVa)

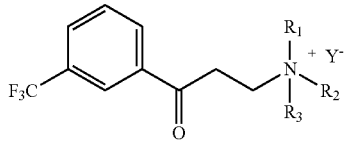

(IVa)

wherein Y=X as defined above, $R_3OCO_2$, $R_3OSO_3$, $(R_3O)_2PO_2$, $CH_3PO_2OR_3$, or $(4-NO_2$—$C_6H_4O)PO_2OR_3$;
d) coupling a compound of formula (IVa) with (R)-(1-naphthyl)ethylamine of formula (III) to give the compound of formula (V)

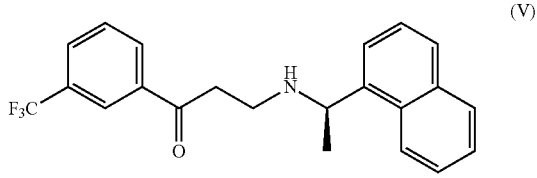 [SMILES: C[C@@H](NCCC(=O)c1cccc(C(F)(F)F)c1)c1cccc2ccccc12]

(V)

It is therefore a still further object of the present invention to provide a method for preparing Cinacalcet hydrochloride of formula (I) as defined above, which further comprises preparing the compound of formula (V), with a process which comprises the above steps b) to d).

For clarity's sake, the above processes for preparing the compound of formula (V) may be illustrated by the following Scheme 3 (corresponding to Scheme 7 of the ZaCh System's co-pending European patent application No. 08167762.7):

Scheme 3

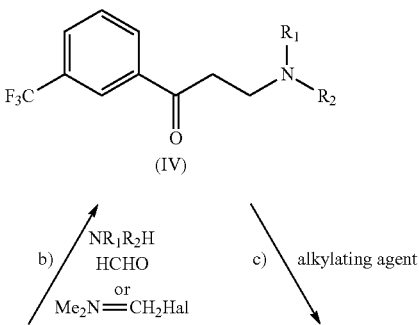

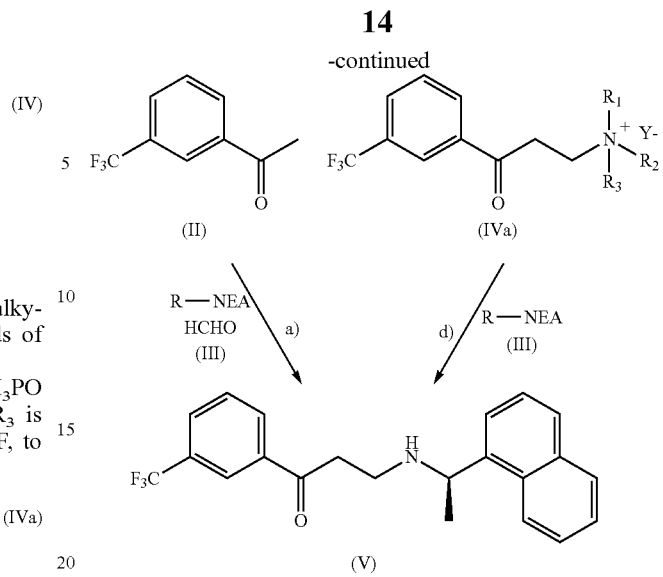

The preparation of the compound of formula (V) according to the above step a) or steps b) to d) can be carried out under the reaction conditions described in ZaCh System's co-pending European patent application No. 08167762.7.

The present invention is exemplified by the following examples, which are provided for illustration only and should not be construed to limit the scope of the invention.

EXAMPLE 1

Synthesis of (R)-3-(1-(naphthalen-1-yl)ethylamino)-1-(3-(trifluoromethyl)phenyl)propan-1-one hydrochloride salt (V)

Method A

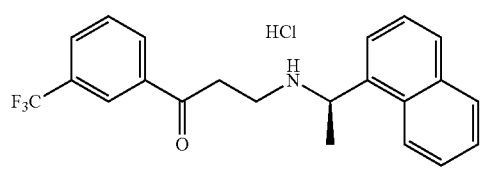 [SMILES: C[C@@H](NCCC(=O)c1cccc(C(F)(F)F)c1)c1cccc2ccccc12 ; Cl]

(R)-(1-naphthyl)ethylamine hydrochloride (III) (100.0 g), paraformaldehyde (15.9 g), 3-(trifluoromethyl)acetophenone (II) (135.7 g), 30% w/w aqueous hydrochloric acid (5.6 g), ethanol (150.0 g) and water (10.0 g) were charged into the reactor and stirred at reflux for 14 hrs, until satisfactory conversion was observed via HPLC. Then water (300.0 g) and toluene (305.0 g) were added and the mixture was stirred at 25° C. The organic and aqueous layers were separated and additional water (200.0 g) was charged over the organic phase in order to favour the precipitation. The title compound (95.6 g) was isolated upon filtration at room temperature, washing with water and methyl tert-butyl ether and exsiccation at 50° C.

Method B (R)-(1-naphthyl)ethylamine hydrochloride (III) (1.5 g), paraformaldehyde (0.3 g), 3-(trifluoromethyl)acetophenone (II) (1.8 g), 30% w/w aqueous hydrochloric acid (0.1 g), ethanol (4.5 g) and water (1.5 g) were charged into the reactor under stirring and reacted for 5 minutes under microwave irradiation (max 250 W), until satisfactory conversion was observed via HPLC. Then water (10.0 g) and toluene (3.0 g) were added and the resulting suspension was stirred at 25° C. The title compound (1.6 g) was isolated upon filtration at room temperature, washing with water and methyl 2-propanol and exsiccation at 50° C.

Method C (R)-(1-naphthyl)ethylamine (III) (82.4 g), paraformaldehyde (15.9 g), 3-(trifluoromethyl)acetophenone (II) (135.7 g), 30% w/w aqueous hydrochloric acid (52.9 g), ethanol (150.0 g) and water (10.0 g) were charged into the reactor and stirred at reflux for 14 hrs, until satisfactory conversion was observed via HPLC. Then water (300.0 g) and toluene (305.0 g) were added and the mixture was stirred at 25° C. The organic and aqueous layers were separated and additional water (200.0 g) was charged over the organic phase in order to favour the precipitation. The title compound (95.6 g) was isolated upon filtration at room temperature, washing with water and methyl tert-butyl ether and exsiccation at 50° C.

NMR of (R)-3-(1-(naphthalen-1-yl)ethylamino)-1-(3-(trifluoromethyl)phenyl) propan-1-one hydrochloride salt (V)

$^1$H NMR (400 MHz, DMSO-d$_6$), δ(ppm, TMS): 10.00 (1H, br s; —NH$_2^+$—), 9.24 (1H, br s; —NH$_2^+$—), 8.31 (1H, d, J=8.4; ArH), 8.23 (1H, d, J=8.0 Hz; ArH), 8.16 (1H, br s; ArH), 8.08-7.96 (4H, m; ArH), 7.82 (1H, t, J=8.0 Hz; ArH), 7.69-7.58 (3H, m; ArH), 5.47-5.36 (1H, m; —CH(CH$_3$)—), 3.70-3.54 (2H, m; —CH$_2$—), 3.41-3.26 (2H, m; —CH$_2$—), 1.72 (3H, m, J=6.4 Hz; —CH(CH$_3$)—).

EXAMPLE 2

Synthesis of 3-(dimethylamino)-1-(3-(trifluoromethyl)phenyl)propan-1-one hydrochloride (IV)

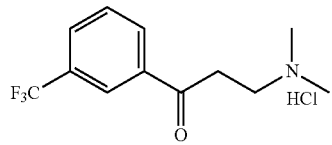 [SMILES: CN(C)CCC(=O)c1cccc(C(F)(F)F)c1 ; Cl]

A mixture of 1-(3-(trifluoromethyl)phenyl)ethanone (25.0 g) (II), dimethylamine hydrochloride (13.0 g), paraformaldehyde (4.8 g), 31% w/w aqueous hydrochloric acid (0.5 mL) in ethanol (70 mL) was stirred at reflux temperature for 24 hrs, then cooled down and the solvent flushed with toluene (50 mL). The precipitated pale yellow solid was then filtrated, washed with toluene and dried to give the title compound (IV) (28.0 g).

EXAMPLE 3

Synthesis of 3-(dimethylamino)-1-(3-(trifluoromethyl)phenyl)propan-1-one hydrochloride (IV)

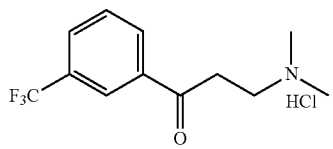 [SMILES: CN(C)CCC(=O)c1cccc(C(F)(F)F)c1 ; Cl]

A mixture of 1-(3-(trifluoromethyl)phenyl)ethanone (5.0 g) (II), N-methyl-N-methylenemethanaminium iodide (5.4 g), 31% w/w aqueous hydrochloric acid (0.1 mL) in ethanol (7 mL) was stirred at reflux temperature for 24 hrs, then cooled down and the solvent flushed with toluene (50 mL). The precipitated pale yellow solid was then filtrated, washed with toluene and dried to give the title compound (IV) (7.1 g).

EXAMPLE 4

Synthesis of N,N,N-trimethyl-3-oxo-3-(3-(trifluoromethyl)phenyl)propan-1-ammonium iodide (IVa)

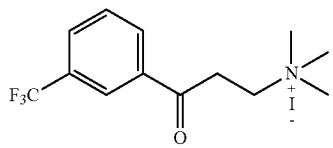

A vigorously stirred biphasic solution of 3-(dimethylamino)-1-(3-(trifluoromethyl)phenyl)propan-1-one (IV) (15.0 g) in a 1:1 water/toluene mixture (50 mL) was added over 1 hr at r.t. with 30% w/w aqueous sodium hydroxide until pH 14. The organic layer was then separated, dried with anhydrous Na$_2$SO$_4$ and filtered. The mother liquor was then charged in a reactor and added, under strong agitation, with methyliodide (22.6 g) in 30 min The mixture was then kept at r.t. for 18 hrs to yield a yellow solid of the methylated Mannich base iodide salt (18.0 g), compound (IVa), that was filtered, dried and used in the following synthetic step without further purification.

EXAMPLE 5

Synthesis of (R)-3-(1-(naphthalen-1-yl)ethylamino)-1-(3-(trifluoromethyl)phenyl)propan-1-one hydrochloride salt (V)

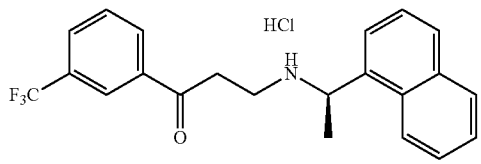 [SMILES: C[C@@H](NCCC(=O)c1cccc(C(F)(F)F)c1)c1cccc2ccccc12 ; Cl]

A vigorously stirred suspension of the methylated Mannich base iodide salt, compound (IVa) (20.5 g), (R)-(1- naphthyl)ethylamine (11.0 g) and potassium carbonate (14.7 g) in acetonitrile (50 mL) was kept at refluxing temperature for 8 hrs, then cooled down to r.t., added with water (20 mL) and extracted twice with ethyl acetate (25 mL). The combined organic phases were then dried and concentrated to give the crude title compound (V) (20.8 g) as yellow oil. Further purification could be achieved upon conversion of the compound (V) into its hydrochloride salt and recrystallization from MTBE.

EXAMPLE 6

Synthesis of (R,E)-N-(1-(naphthalen-1-yl)ethyl)-3-(3-(trifluoromethyl)-phenyl)prop-2-en-1-amine (CNC-ene free base)

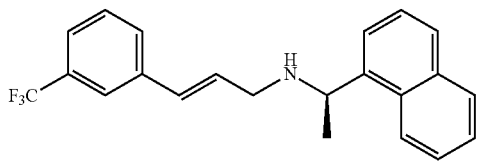 [SMILES: C[C@@H](NC/C=C/c1cccc(C(F)(F)F)c1)c1cccc2ccccc12]

The diastereoisomeric mixture of (R) and (S)-3-((R)-1-(naphtalen-1-yl)ethylamino-1-(3-(trifluoromethyl)phenyl) propan-1-ol (obtained following the teachings of Example 7 of ZaCh System's co-pending European patent application No. 08167762.7) was charged into the reactor as a toluene solution (33.7 g). Acetic acid (76.9 g) and concentrated sulphuric acid (96% w/w; 49.0 g) were then added slowly at 25° C., the reaction mixture was heated at 110° C. for 1 hr, then cooled down to 5° C. The mass was diluted by addition of toluene (85.0 g) and, dropwise, water (50.0 g), then stirred at 25° C. for few minutes. The organic and aqueous phases were separated and the toluene layer was cooled to 5° C. and neutralized by addition of aqueous ammonia (28% w/w; 40.0 g) up to pH 10. Once room temperature was reached, water (30.0 g) was added in order to solubilise salts, the phases were separated and the solvent was removed form the organic layer via reduced pressure distillation. The crude title compound was obtained as a pale yellow oil (17.7 g).

NMR of (R,E)-N-(1-(naphthalen-1-yl)ethyl)-3-(3-(trifluoromethyl)phenyl)prop-2-en-1-amine $^1$H NMR (400 MHz, CDCl$_3$), δ(ppm, TMS): 8.21-8.17 (1H, m; ArH), 7.92-7.86 (1H, m; ArH), 7.78 (1H, d, J=8.0 Hz; ArH), 7.72 (1H, d, J=7.2 Hz; ArH), 7.58-7.45 (6H, m; ArH), 7.43-7.37 (1H, m; ArH), 6.48 (1H, d, J=16.0 Hz; —ArCH=CHCH$_2$—), 6.39 (1H, dt, J=6.0, 6.0 Hz; —ArCH=CHCH$_2$—), 4.76 (1H, q, J=6.6 Hz; —CH(CH$_3$)—), 3.46-3.33 (2H, m; —CH$_2$—), 1.57 (3H, d, J=6.6; —CH(CH$_3$)—).

EXAMPLE 7

Synthesis of (R,E)-N-(1-(naphthalen-1-yl)ethyl)-3-(3-(trifluoromethyl)-phenyl)prop-2-en-1-amine hydrochloride salt (VIIa)

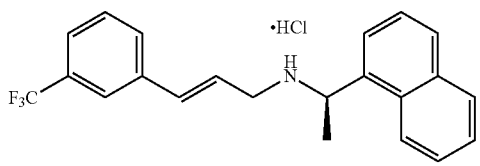 [SMILES: C[C@@H](NC/C=C/c1cccc(C(F)(F)F)c1)c1cccc2ccccc12 ; Cl]

(R,E)-N-(1-(naphthalen-1-yl)ethyl)-3-(3-(trifluoromethyl)phenyl)prop-2-en-1-amine (CNC-ene free base) (4.3 g, 12.122 mmol) is diluted with MTBE (50 ml) and added with 1.20 equiv. of 31% w/w aqueous hydrochloric acid. Excess water is removed by azeotropic distillation. The organic phase is then concentrated up to 60% volume and the so formed precipitate is isolated upon cooling down to 0° C. and filtering. Vacuum drying affords 4.6 g of a white powder (VIIa; 11.739 mmol, 96.8% yield).

EXAMPLE 8

Synthesis of (R,E)-N-(1-(naphthalen-1-yl)ethyl)-3-(3-(trifluoromethyl)phenyl)prop-2-en-1-amine HZ salts (VIIc) (VIId) (VIIe)

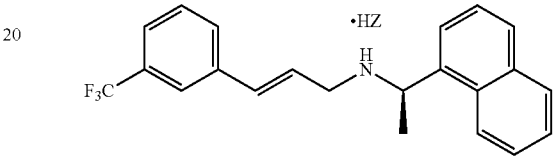

(VIIc)=(VII) wherein Z=tartrate;
(VIId)=(VII) wherein Z=succinate;
(VIIe)=(VII) wherein Z=p-toluenesulfonate (R,E)-N-(1-(naphthalen-1-yl)ethyl)-3-(3-(trifluoromethyl)phenyl)prop-2-en-1-amine (CNC-ene free base) (4.3 g, 12.122 mmol) is diluted with MTBE (50 ml) and added with 1.05 equiv. of the acid HZ (where HZ: (c)=meso-tartaric acid, (d)=succinic acid, and (e)=p-toluenesulfonic acid). Filtration of the so formed precipitate and vacuum drying affords the corresponding (R,E)-N-(1-(naphthalen-1-yl)ethyl)-3-(3-(trifluoromethyl)phenyl)prop-2-en-1-amine salts (VIIc), (VIId) or (VIIe), with yields ranging from (VIIc) 27.6% (white powder), to (VIId) 69.7% (white powder) and (VIIe) 94.5% (white powder).

EXAMPLE 9

Conversion of (R,E)-N-(1-(naphthalen-1-yl)ethyl)-3-(3-(trifluoromethyl)phenyl)prop-2-en-1-amine HZ salt (VIIe) into (R,E)-N-(1-(naphthalen-1-yl)ethyl)-3-(3-(trifluoromethyl)phenyl)prop-2-en-1-amine hydrochloride salt (VIIa)

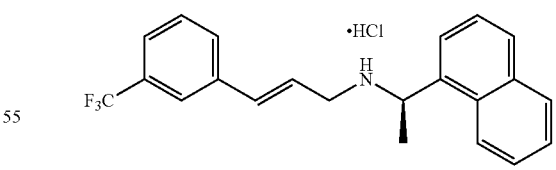

(VIIe)=(VII) wherein Z=p-toluenesulfonate (R,E)-N-(1-(naphthalen-1-yl)ethyl)-3-(3-(trifluoromethyl)phenyl)prop-2-en-1-amine p-toluenesulfonate (VIId) is free-based by addition of 30% w/w aqueous NaOH in a MTBE/water mixture at 25° C. up to pH 12 of the aqueous layer. The organic layer is then separated and acidified with 31% w/w aq. HCl (1.2 equiv.) up to pH 1 in the aqueous layer. The aqueous layer is separated and residual water is stripped out of the organic phase by azeotropic distillation.

Once water is completely removed the organic solvent is distilled off (T=54°-55° C., P=900 mbar) until a 40% reduction of the total volume is achieved. The mixture is then cooled down to 0° C. and filtered. (R,E)-N-(1-(naphthalen-1-yl)ethyl)-3-(3-(trifluoromethyl)phenyl)prop-2-en-1-amine hydrochloride salt (VIIa) is obtained as a white powder, with isolated yields of 87.1%.

EXAMPLE 10

Synthesis of (R) and (S)-3-((R)-1-(naphthalen-1-yl)ethylammonio)-1-(3-(trifluoromethyl)phenyl)propyl sulfate (VIII)

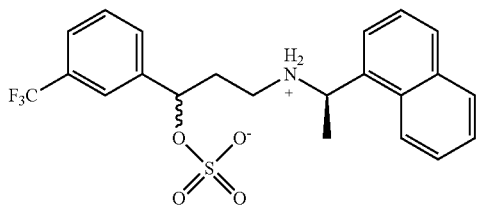

(R)-3-(1-(naphthalen-1-yl)ethylamino)-1-(3-(trifluoromethyl)phenyl)propan-1-one hydrochloride salt (V) (150.0 g, 365.934 mmol) is suspended in cold methanol (570 ml) at −5°-0° C. and a solution of NaBH$_4$ (6.3 g, 166.534 mmol, 0.45 equiv.), 30% aq. NaOH (53.8 g, 403.500 mmol, 1.1 equiv.) in water (45 ml) is slowly added over 30 minutes. Once the reaction is complete (IPC via HPLC) acetic acid (55.0 g, 913.903 mmol, 2.5 equiv.) is charged slowly, keeping the internal temperature below 5° C., followed by water (415 ml). The reaction mixture is then heated up to 50° C. and the solvent is distilled off under reduced pressure to half volume. After that, isopropyl ether (450 ml) is charged, the mixture is stirred and, once layered, the lower phase is separated. The organic phase is washed with water (75 ml), then MTBE (400 ml) is added and washed again with water (3×75 ml). Thus, volatile solvents are flushed with isopropyl ether and residual water removed azeotropically. Acetonitrile (300 ml) is added at 10° C. and concentrated sulphuric acid (35.5 g, 347.507 mmol) is charged slowly, followed by acetic anhydride (71.0 g, 695.275 mmol) at 20°-25° C. The reaction mixture is stirred at 20°-25° C. for about 1 hour, until complete conversion is observed via HPLC, then cooled down to 0° C. The resulting precipitate is isolated by filtration and washed with isopropyl ether (3×65 ml) and dried under vacuum at 55° C. The title compound (VIII) (152.9 g, 302.314 mmol) is obtained in 82.6% yield.

EXAMPLE 11

Synthesis of (R,E)-N-(1-(naphthalen-1-yl)ethyl)-3-(3-(trifluoromethyl)phenyl)prop-2-en-1-amine HZ salt (VIIb)

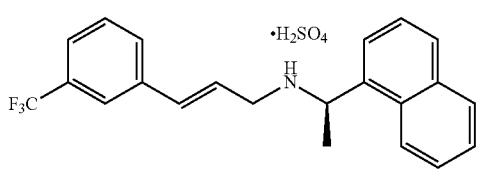 [SMILES: C[C@@H](NC/C=C/c1cccc(C(F)(F)F)c1)c1cccc2ccccc12 ; "·H2SO4"]

(VIIb)=(VII) wherein Z=bisulfate

A 500 ml reactor is loaded with (R) and (S)-3-((R)-1-(naphthalen-1-yl)ethylammonio)-1-(3-(trifluoromethyl)phenyl)propyl sulfate (VIII) (55.0 g, 121.287 mmol) and n-butyl acetate (250 ml), and 96% H$_2$SO$_4$ (37.1 g, 363.169 mmol, 3.0 equiv.) is added dropwise at room temperature. The reaction mixture is heated up to 115° C. and stirred for 15 hours, then cooled down to 15° C. The reaction mixture is washed with water (2×110 ml), 6% w/w aq. NaOH (139.2 g) and 8% w/w aq. NaHCO$_3$ (110.0 g). The organic solution is then treated with charcoal and filtered, washed with water (2×55 ml) and added with n-butyl acetate up to 400 ml total volume. The solvent is then distilled off up to half volume. The organic solution is added with n-butyl acetate (170 ml) and acidified with 96% w/w H$_2$SO$_4$ (11.2 g, 109.636 mmol). The resulting suspension is heated up to 90° C. and stirred until a clear solution is obtained (1 hour). The solution is cooled down to 65° C. and maintained until precipitation is observed, then cooled to 0° C. over 30 mins. The solid is filtered, washed with cold n-butyl acetate and dried at 50° C. under vacuum. The title compound (VIIb) (37.1 g, 81.814 mmol, 67.5% yield) is obtained as a white powder.

EXAMPLE 12

Conversion of (R,E)-N-(1-(naphthalen-1-yl)ethyl)-3-(3-(trifluoromethyl)phenyl)prop-2-en-1-amine bisulfate salt (VIIb) into (R,E)-N-(1-(naphthalen-1-yl)ethyl)-3-(3-(trifluoromethyl)phenyl)prop-2-en-1-amine hydrochloride salt (VIIa)

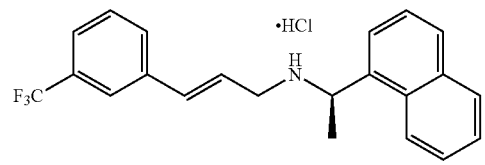 [SMILES: C[C@@H](NC/C=C/c1cccc(C(F)(F)F)c1)c1cccc2ccccc12 ; Cl]

Method A (R,E)-N-(1-(naphthalen-1-yl)ethyl)-3-(3-(trifluoromethyl)phenyl)prop-2-en-1-amine bisulfate salt (VIIb) (55.1 g, 121.466 mmol) is free-based by addition of 30% w/w aqueous NaOH (34.8 g, 261.0 mmol, 2.2 equiv.) in a methyl tert-butyl ether (MTBE)/water mixture at 25° C., up to pH 12 of the aqueous layer. The organic layer is then separated and acidified with 31% w/w aq. HCl (17.6 g, 149.643 mmol, 1.2 equiv.) up to pH 1 in the aqueous layer. The aqueous layer is separated and residual water is stripped out of the organic phase by azeotropic distillation (T=54°). Once water is completely removed a white precipitate is formed and the organic solvent is distilled off (T=54°-55° C., P=900 mbar) until a 40% reduction of the total volume is achieved. The slurry is then cooled down to 0° C. and filtered. (R,E)-N-(1-(naphthalen-1-yl)ethyl)-3-(3-(trifluoromethyl)phenyl)prop-2-en-1-amine hydrochloride salt (VIIa) (46.7 g, 119.175 mmol, 98.1% yield) is obtained as a white powder (HPLC assay: 99.5% w/w).

Method B (R,E)-N-(1-(naphthalen-1-yl)ethyl)-3-(3-(trifluoromethyl)phenyl)prop-2-en-1-amine bisulfate salt (VIIb) (5.0 g, 11.026 mmol) is dissolved in a hot water/2-propanol mixture 7:3 vol/vol (55 mL). The solution is then added with concentrated hydrochloric acid (6.5 g, 55.521 mmol) and cooled down slowly to 25° C. A white precipitate is formed, the slurry is filtered and the solid washed with water. (R,E)-N-(1-(naphthalen-1-yl)ethyl)-3-(3-(trifluoromethyl)phenyl)prop-2-en-1-amine hydrochloride salt (VIIa) (3.9 g, 9.953 mmol, 90.3%% yield) is obtained as a white powder.

EXAMPLE 13

Synthesis of Cinacalcet hydrochloride (I) from (R,E)-N-(1-(naphthalen-1-yl)ethyl)-3-(3-(trifluoromethyl)phenyl)prop-2-en-1-amine hydrochloride salt (VIIa)

A mixture of (R,E)-N-(1-(naphthalen-1-yl)ethyl)-3-(3-(trifluoromethyl)phenyl)prop-2-en-1-amine hydrochloride salt (VIIa) (5.0 g) and palladium catalyst (0.0005-0.01 equiv.) in alcoholic solvent or in alcohol/ester mixtures (30-50 mL) is pressurized with 1 bar hydrogen and stirred at +20° C. The mixture is then filtered through a Celite® pad and concentrated in order to give Cinacalcet hydrochloride (I) which is optionally recrystallized from ether or ester solvents or mixtures thereof (see the following table for detailed results).

| Catalyst | % Cat, mol/mol | Solvent, v/v | Time, hrs | Conversion, % | Isolated Yield, % |
|---|---|---|---|---|---|
| PdCl$_2$ | 1.0 | EtOAc/MeOH 1:1 | 10 | 100.0 | 92.0 |
| PdCl$_2$ | 1.0 | EtOAc/MeOH 1:1 | 0.5 | 100.0 | 92.5 |
| PdCl$_2$ | 0.6 | iPrOH/MeOH 3:1 | 96 | 99.8 | 80.5 |
| PdCl$_2$ | 1.0 | EtOAc/MeOH 1:1 | 28 | 99.9 | 88.0 |
| Pd/C | 0.5 | EtOAc/MeOH 1:1 | 1 | 99.8 | 90.0 |
| Pd/C | 0.15 | EtOAc/MeOH 1:1 | 2 | 99.9 | 90.0 |
| Pd/C | 0.05 | EtOAc/MeOH 1:1 | 5 | 99.8 | 90.0 |
| Pd/C | 0.05 | EtOH | 9 | 99.9 | 90.0 |
| Pd/C | 0.05 | MeOH | 9 | 99.9 | 90.0 |

EXAMPLE 14

Synthesis of N-[(1R)-1-(1-naphthyl)ethyl]-3-[3-(trifluoromethyl)phenyl]propan-1-amine HZ salt (Ia) wherein Z=bisulfate (Cinacalcet bisulfate) from (R,E)-N-(1-(naphthalen-1-yl)ethyl)-3-(3-(trifluoromethyl)phenyl)prop-2-en-1-amine bisulfate salt (VIIb)

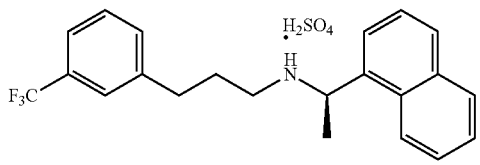 [SMILES: C[C@@H](NCCCc1cccc(C(F)(F)F)c1)c1cccc2ccccc12 ; "H2SO4"]

A mixture of (R,E)-N-(1-(naphthalen-1-yl)-ethyl)-3-(3-(trifluoromethyl)-phenyl)prop-2-en-1-amine bisulfate salt (VIIb) (5.0 g) and 5% palladium on carbon (0.0005 equiv.) in ethyl acetate/methanol 1:1 vol/vol (40 ml) is pressurized with 1 bar hydrogen and stirred at +20° C. for 10 hours. The mixture is then filtered through a Celite® pad and concentrated in order to give Cinacalcet bisulfate, which is recrystallized from ether or ester solvents or mixtures thereof, affording 84.0% yield.

EXAMPLE 15

Conversion of Cinacalcet bisulfate into Cinacalcet hydrochloride (I)

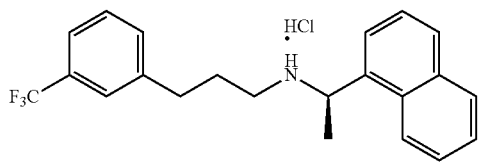 [SMILES: C[C@@H](NCCCc1cccc(C(F)(F)F)c1)c1cccc2ccccc12 ; Cl]

Cinacalcet bisulfate (1.0 g, 2.200 mmol) is dissolved in a hot water/2-propanol mixture (12-14 mL). The solution is then cooled down to 20° C. and concentrated hydrochloric acid (1.0 g, 8.493 mmol) is added. A white precipitate is formed, the slurry is filtered and the solid washed with water. Cinacalcet hydrochloride (I) (0.7 g, 1.777 mmol, 80.8% yield) is obtained as a white powder. (HPLC assay: 99.5% w/w).

The invention claimed is:
1. A method for preparing Cinacalcet hydrochloride of formula (I)

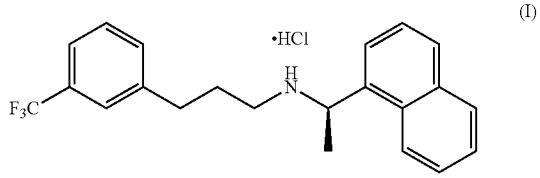 [SMILES: C[C@@H](NCCCc1cccc(C(F)(F)F)c1)c1cccc2ccccc12 ; Cl]

which comprises the steps of:
e) reducing a compound of formula (VII)

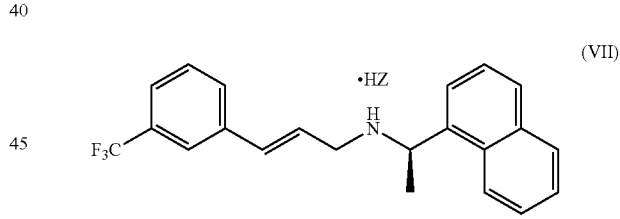

wherein Z is chloride or another pharmaceutically acceptable anionic counterion, to obtain a compound of formula (Ia)

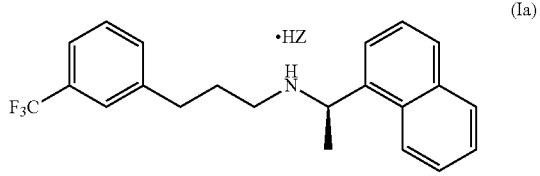

wherein Z is as defined above and, when in a compound of formula (Ia) Z is a pharmaceutically acceptable anionic counterion different from chloride,
f) converting said compound of formula (Ia) to Cinacalcet hydrochloride of formula (I), wherein when in the compound of formula (VII) Z is chloride, the compound has formula (VIIa)

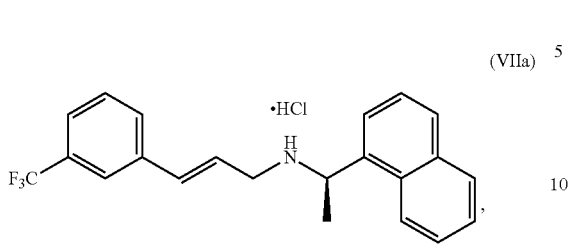

said compound of formula (VIIa) being obtained with a process comprising the step of:

g) converting a compound of formula (VII)

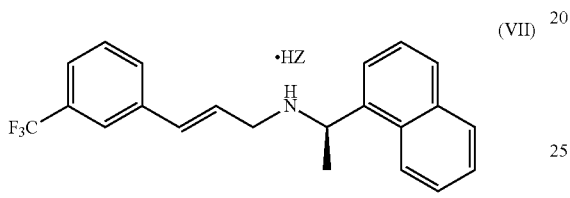

wherein Z is a pharmaceutically acceptable anionic counterion different from chloride;
said compound of formula (VII), wherein Z is a pharmaceutically acceptable anionic counterion different from chloride, being obtained with a process comprising the step of:
j) eliminating sulfuric acid from the compound of formula (VIII)

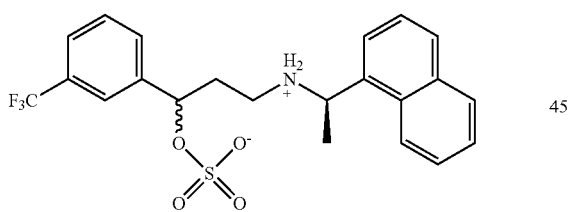

wherein the wavy line represents a bond connected to carbon having R or S configuration, with a strong acid, neutralizing and acidifying with an acid HZ, wherein Z is a pharmaceutically acceptable anionic counterion different from chloride.

2. A method according to claim 1, wherein the pharmaceutically acceptable anionic counterion different from chloride is selected from bromide, bisulfate, methanesulfonate, p-toluenesulfonate, phosphate, hydrogenphosphate, oxalate, formate, acetate, citrate, tartrate, succinate, maleate and malonate.

3. A method according to claim 1, wherein in a compound of formula (VII), Z is different from chloride.

4. A method according to claim 1, wherein in the compound of formula (VII) Z is bisulfate, namely it is a compound of formula (VIIb)

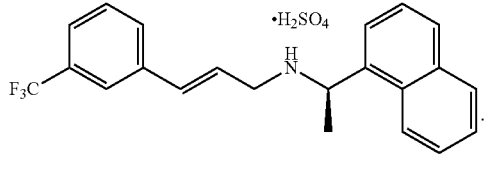

5. A method according to claim 1, wherein the strong acid is sulfuric or phosphoric acid.

6. A method according to claim 1, wherein the acid HZ is $H_2SO_4$.

7. A method according to claim 1, which further comprises obtaining the compound of formula (VIII), with a process which comprises the steps of k) reducing the compound of formula (V)

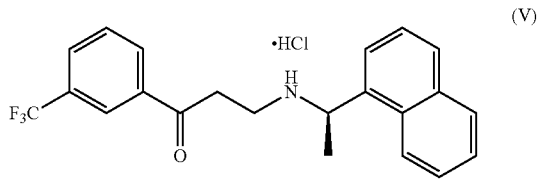 [SMILES: C[C@@H](NCCC(=O)c1cccc(C(F)(F)F)c1)c1cccc2ccccc12 ; Cl]

to the corresponding benzylic alcohol of formula (Va)

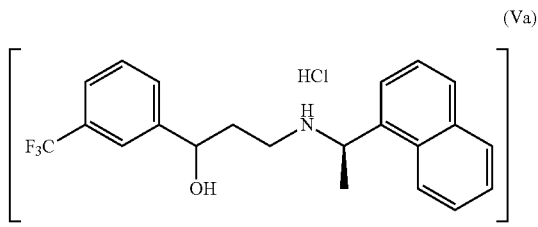

wherein [ ] means that the compound of formula (Va) can be isolated or not from the reaction mixture, in the presence of a reducing agent or by mean of a catalytic hydrogenation process, and l) converting the compound of formula (Va) into the sulfate ester of formula (VIII).

8. A method according to claim 7, which further comprises obtaining the compound of formula (V), with a process which comprises the steps of:

a) reacting 3-trifluoromethyl)acetophenone of formula (II)

with (R)-(1-naphthyl)ethylamine of formula (III) optionally in the hydrochloride form,

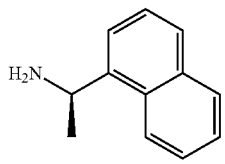

(III)

in the presence of formaldehyde and hydrochloric acid.

9. A method according to claim 7, which further comprises obtaining the compound of formula (V), with a process which comprises the steps of:

b) reacting the compound of formula (II)

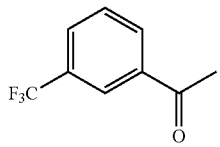

(II)

(i) with a compound of formula

HNR₁R₂, wherein R₁ and R₂ represent, independently, hydrogen or C₁-C₅alkyl, provided that when one of R₁ and R₂ is hydrogen, the other is not hydrogen; or wherein R₁ and R₂ together form a C₄-C₇ alkyl bridge, so that with the inclusion of the nitrogen atom to which they are linked a heterocycle is formed, wherein one —CH₂— group of the C₄-C₇ alkyl bridge, can be replaced by —O—, in the presence of formaldehyde; or (ii) with a N-methyl-N-methylenemethanaminium halide of formula

(CH₃)₂N=CH₂ Hal⁻ wherein Hal is a halogen atom, to obtain the compound of formula (IV)

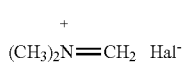

(IV)

wherein R₁ and R₂ are as defined above;

c) alkylating the compound of formula (IV) with an alkylating agent selected from the group of compounds of formula:

R₃—X, CO(OR₃)₂, SO₂(OR₃)₂, PO(OR₃)₃, CH₃PO(OR₃)₂ and (4-NO₂C₆H₄O)PO(OR₃)₂, wherein R₃ is C₁-C₄ alkyl and X is I, Br, OSO₂CF₃ or OSO₂F, to obtain a compound of formula (IVa)

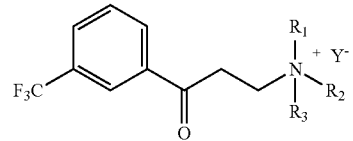

(IVa)

wherein Y=X as defined above, R₃OCO₂, R₃OSO₃, (R₃O)₂PO₂, CH₃PO₂OR₃, or (4-NO₂—C₆H₄O)PO₂OR₃; and d) coupling a compound of formula (IVa) with (R)-(1-naphthyl)ethylamine of formula

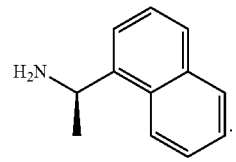

(III)

10. A method for preparing Cinacalcet intermediate of formula (VIII)

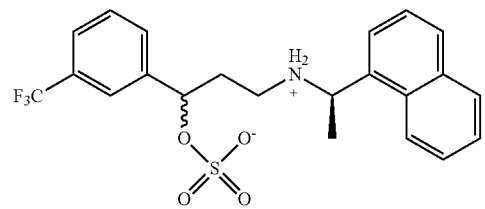

(VIII)

wherein the wavy line represents a bond connected to carbon having R or S configuration, which comprises the steps of:

k) reducing the compound of formula (V)

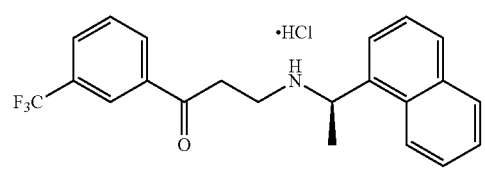

(V)

to the corresponding benzylic alcohol of formula (Va)

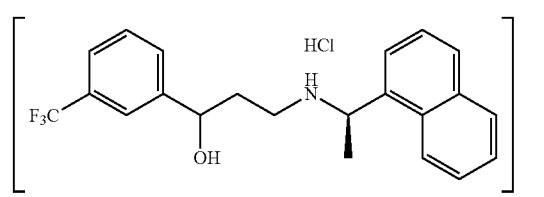

(Va)

wherein [ ] means that the compound of formula (Va) can be isolated or not from the reaction mixture, in the presence of a reducing agent or by mean of a catalytic hydrogenation process, and l) converting the compound of formula (Va) in the sulfate ester of formula (VIII).

11. A method for preparing Cinacalcet hydrochloride of formula (I)

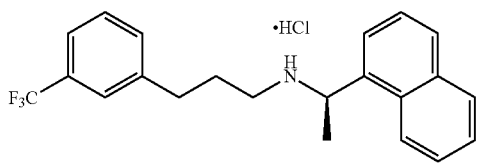

which comprises the steps of
k) reducing the compound of formula (V)

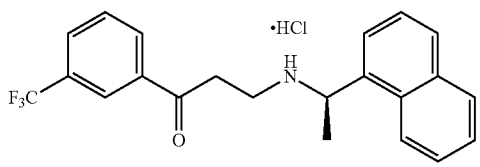

to the corresponding benzylic alcohol of formula (Va)

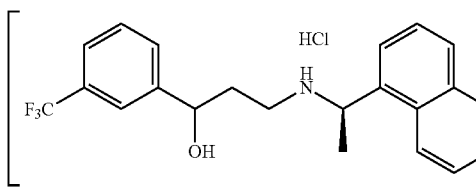

wherein [ ] means that the compound of formula (Va) can be isolated or not from the reaction mixture, in the presence of a reducing agent or by mean of a catalytic hydrogenation process,
l) converting the compound of formula (Va) into the sulfate ester of formula (VIII)

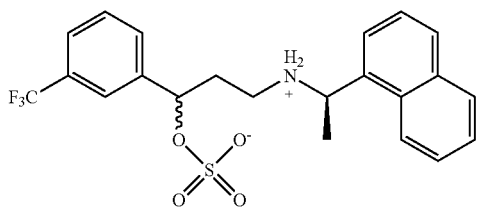

wherein the wavy line represents a bond connected to carbon having R or S configuration, j) eliminating sulfuric acid from the compound of formula (VIII) with a strong acid, neutralizing and acidifying with the $H_2SO_4$ to give the compound of formula (VIIb)

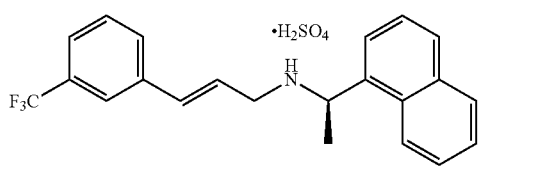

g) converting the compound (VIIb) into the compound (VIIa) and

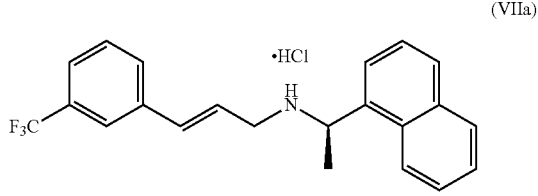 [SMILES: C[C@@H](NC/C=C/c1cccc(C(F)(F)F)c1)c1cccc2ccccc12 ; Cl]

e) reducing the compound (VIIa) to Cinacalcet hydrochloride of formula (I).

12. Cinacalcet intermediate having the following formula (VIII)

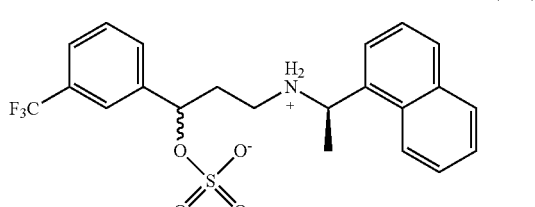

wherein the wavy line represents a bond connected to carbon having R or S configuration.

* * * * *